(12) United States Patent
Schewiola et al.

(10) Patent No.: US 9,905,323 B2
(45) Date of Patent: Feb. 27, 2018

(54) CONTOUR COLLIMATOR FOR RADIOTHERAPY

(71) Applicant: Deutsches Krebsforschungszentrum, Heidelberg (DE)

(72) Inventors: Klaus Schewiola, Heidelberg (DE); Steffen Seeber, Heidelberg (DE)

(73) Assignee: DEUTSCHES KREBSFORSCHUNGSZENTRUM, Heidelberg (DE)

( * ) Notice: Subject to any disclaimer, the term of this patent is extended or adjusted under 35 U.S.C. 154(b) by 34 days.

(21) Appl. No.: 14/778,353

(22) PCT Filed: Mar. 18, 2014

(86) PCT No.: PCT/EP2014/055360
§ 371 (c)(1),
(2) Date: Sep. 18, 2015

(87) PCT Pub. No.: WO2014/147046
PCT Pub. Date: Sep. 25, 2014

(65) Prior Publication Data
US 2016/0071623 A1   Mar. 10, 2016

(30) Foreign Application Priority Data
Mar. 22, 2013 (EP) .................... 13160589

(51) Int. Cl.
*G21K 1/04* (2006.01)
(52) U.S. Cl.
CPC .................... *G21K 1/046* (2013.01)
(58) Field of Classification Search
CPC ...... A61B 6/06; A61N 5/1042; A61N 5/1045; G21K 1/04; G21K 1/046
See application file for complete search history.

(56) References Cited

U.S. PATENT DOCUMENTS

| 4,794,629 A | 12/1988 | Pastyr et al. |
| 6,052,430 A | 4/2000 | Siochi et al. |

(Continued)

FOREIGN PATENT DOCUMENTS

| CN | 1975581 A | 6/2007 |
| CN | 101013094 A | 8/2007 |

(Continued)

OTHER PUBLICATIONS

U.S. Appl. No. 61/769,549, filed Feb. 26, 2013, cited as a priority document on the front face of Orton (US 2014/0239204 A1).*

(Continued)

*Primary Examiner* — Thomas R Artman
(74) *Attorney, Agent, or Firm* — Foley & Lardner LLP

(57) ABSTRACT

The invention relates to a contour collimator for radiotherapy, comprising a plurality of plate-shaped diaphragm elements provided in a guiding block and movably arranged with respect to one another to form a contour diaphragm for a radiation beam emitted by a radiation source towards the collimator, and at least one drive for moving the diaphragm elements, wherein a drive of its own is associated with each diaphragm element, the drives of a group of diaphragm elements are arranged substantially adjacent to one another, and the drive is a linear motor, wherein each linear motor comprises a linearly movable rod directly fixed to the associated diaphragm element. The invention facilitates a design of a contour collimator with a shape being as compact as possible, and wherein both precise and stable adjustability of the diaphragm elements is achieved without a backlash. In this way improvements to contour collimators are provided.

8 Claims, 6 Drawing Sheets

(56) References Cited

U.S. PATENT DOCUMENTS

Figure 1:
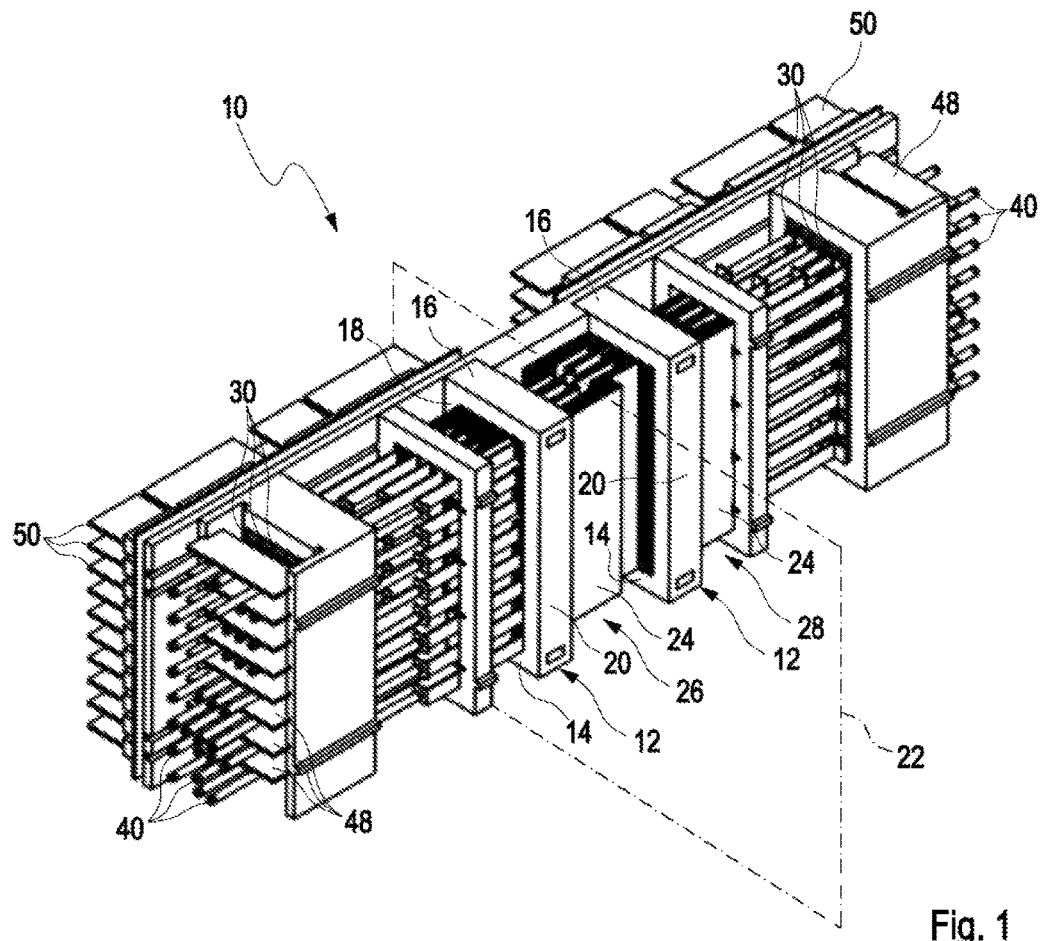

| | | | |
|---|---|---|---|
| 6,188,748 B1 | 2/2001 | Pastyr et al. | |
| 6,891,177 B1 | 5/2005 | Kraft et al. | |
| 7,242,750 B2 | 7/2007 | Tsujita | |
| 7,262,423 B2 | 8/2007 | Van Herpen et al. | |
| 7,429,738 B2 | 9/2008 | Li et al. | |
| 2004/0062354 A1* | 4/2004 | Kato | A61N 5/1042 378/152 |
| 2008/0191583 A1 | 8/2008 | Bohn | |
| 2010/0278310 A1 | 11/2010 | Dehler et al. | |
| 2014/0217312 A1* | 8/2014 | Echner | G21K 1/046 250/505.1 |
| 2014/0239204 A1* | 8/2014 | Orton | G21K 1/046 250/505.1 |

FOREIGN PATENT DOCUMENTS

| | | |
|---|---|---|
| CN | 102103091 A | 6/2011 |
| DE | 199077098 A1 | 8/2000 |
| WO | WO 2012/123093 A1 | 9/2012 |

OTHER PUBLICATIONS

International Preliminary Report on Patentability issued in related International Patent Application No. PCT/EP2014/055360, dated Oct. 1, 2015.

International Search Report issued in related International Patent Application No. PCT/EP2014/055360, dated May 9, 2014.

Chinese Office Action issued in related Chinese Patent Application No. 201480029022.9, dated Nov. 23, 2016 (including partial translation).

* cited by examiner

CONTOUR COLLIMATOR FOR RADIOTHERAPY

CROSS-REFERENCE TO RELATED APPLICATIONS

This application is a National Phase of PCT/EP2014/055360, filed Mar. 18, 2014, which claims priority from European Patent Application No. 13160589.1, filed Mar. 22, 2013. The contents of these applications are incorporated herein by reference in their entirety.

The present invention relates to a contour collimator for radio therapy comprising a plurality of diaphragm elements provided in a guiding block and movably arranged with respect to one another to form a contour diaphragm for a radiation beam emitted by a radiation source towards the collimator, and at least one drive for moving the diaphragm elements, wherein a drive of its own is associated with each diaphragm element, the drives of a group of diaphragm elements are arranged substantially adjacent to one another, and a driving transmission of its own is provided between each drive and the associated diaphragm element.

Usually, the diaphragm elements are shaped or formed as leaves. Various embodiments of multi-leaf collimators comprising diaphragm elements leaf modules each featuring a leaf unit and a leaf drive unit are known in the art. Multi-leaf collimators of such kind are preferably employed for controlling a shape of a high-energy radiation beam emanating from a radiation source and propagating in a direction of propagation.

Multi-leaf collimators are commonly used in treatment devices for oncological radiation therapy. Said collimators delimit high-energy beams, in most cases high energy radiation of a linear accelerator, in such a way that the beams have exactly the same shape as the treatment object. Since such irradiation, e.g. of a tumor, occurs from various directions, it is possible to achieve a great irradiation intensity of the tumor and, at the same time, to stress the surrounding tissue only to a limited extent.

The diaphragm elements or leaves of the multi-leaf collimator may also be called "shutter blades" or "lamellae". The multi-leaf collimators may also be called contour collimators since due to the positioning of the leaves, contours of treatment objects, for example tumors, can be recreated for each beam application, each of which occurs from a certain solid angle. This is important in order to protect the adjacent healthy tissue to the greatest extent possible. In the case of organs at risk, such as spine or nerves, this is particularly necessary in order to preserve their functional capability.

A general example of a multi-leaf collimator comprising leaf modules with a leaf unit and a leaf drive unit is obtainable from U.S. Pat. No. 4,794,629. In such multi-leaf collimators, each leaf unit must be moved into a certain position. Thus, in most cases, a leaf drive unit must be assigned to each leaf unit. According to the aforementioned publication, no separate motor is assigned to each leaf unit, which is why the leaf units are arranged in series by means of drive couplings and locking devices. However, it has also been known to assign an electric motor to each leaf unit that positions the leaf unit via a pinion and a gear rod-like drive engagement.

However, the more precisely the shape of the treatment object, e.g. of a tumor, is to be recreated, the more and thinner leaves within the leaf units will be required. This means that a large number of electric motors and drive transmissions within the leaf drive units being connected to the leaf units must be housed in an extremely small space. Also, the leaf modules are arranged in such manner that they will be located within one irradiation head containing the radiation source and the collimator.

During an irradiation treatment, the irradiation head usually has to be moved into various but defined angles with respect to the target volume, e.g. the tumor. Thus, it is desirable to design such a collimator as compact and lightweight as possible.

Further, when designing leaf modules for a multi-leaf collimator, the accuracy of the adjusting, i.e. the displacement of the leaf units in the adjusting direction with relation to the leaf drive unit, is a decisive factor both for therapeutic success of the irradiation treatment and for possible adverse effects due to misguided irradiation.

Several proposals have been made to employ drive mechanisms operating based on piezoelectric actuation within leaf drive units of leaf modules. General advantages of piezoelectric actuation, in particular by piezoelectric motors, may be identified as the high dynamics, the high positioning accuracy and the low impact of noise within the human acoustic range. Furthermore, piezoelectric motors may exert a clamping force on adjacent parts even when not being in operation. Also, piezoelectric motors do not emit a disruptive magnetic field as conventional electric motors do. This advantage particularly applies to the novel technique of combining imaging by magnetic resonance and radiation therapy with linear acceleration (MR-Linac). In this regard, the strong magnetic field established by the MRT will not disrupt conventional electric motors, as these are replaced by piezoelectric actuation. On the other hand, piezoelectric motors will not build a magnetic field disrupting the MR-imaging and/or the linear acceleration.

US 2010/0278310 A1 discloses a multi-leaf collimator with rotatory electromechanical motor and operating method. The electromechanical motor may be a piezo motor. The piezo motor engages leaf units by means of a toothing in order to displace the leaf units. However, indirect transmission of the piezo motor actuation via the proposed toothing involves a backlash concerning the accuracy of displacement of the leaf unit. Furthermore, inevitable slackness within the toothed transmission represents a further major backlash. When the irradiation head is moved in the manner described above, variations in the position of the irradiation head result in changes to the adjusting position of the leaf units, because the weight of the leaf units interacting with the slackness in the toothing within the transmission and/or within the guidance of the leaf unit displacement will result in unwanted deviation of leaf unit adjustment.

U.S. Pat. No. 7,242,750 B2 discloses a radiotherapy apparatus comprising a radiation source configured to radiate a radiation ray, a multi-leaf collimator, including a plurality of leaves, configured to limit a radiation range of the radiation ray and a drive unit configured to move at least one of the leaves with an ultrasonic wave. However, this publication does not explicitly address the disadvantageous effects of slackness within the transmission and/or guiding between leaf drive unit and leaf unit as observed in the course of the present invention and as described above.

A linear drive and a method for displacing an object by a linear drive, wherein the linear drive comprises at least one piezoelectric actuator, has been proposed by US 2008/0191583 A1.

U.S. Pat. No. 6,188,748 B1 discloses a contour collimator of the kind mentioned at the beginning of this specification.

The contour collimator according to U.S. Pat. No. 6,188,748 B1 employs a linear drive, wherein a driving transmission is provided between each drive and the associated diaphragm element. The driving transmission has a flexible but tension resistant and pressure resistant power transmitting element one end of which is connected with the diaphragm element and the other end of which is connected with the associated drive. The drive comprises a gear which transmits a rotational movement of the drive to the transmitting element.

However, the connection of the transmitting element with the diaphragm element and the associated drive requires coupling elements which increases the costs for manufacturing the collimator. Further, transmission gears are needed for driving the diaphragm elements. When moving the diaphragm elements, a mechanical backlash inevitably occurs. Thus, the dynamic behavior and the motion speed are rather low. Still further, an additional position sensor is required for detecting the exact position of the diaphragm elements as the mechanical friction may cause deviations from the target position. The frictional force sectionally applied by the transducer to the diaphragm element may also result in lateral displacement of the diaphragm element in a direction being oriented perpendicularly related to the adjusting direction. Further linear guiding of the diaphragm element has to be provided, resulting in further frictional force and thus in inaccuracy of adjustment.

The invention is therefore based on the objective of designing a contour collimator of the kind mentioned at the beginning in such a way that with a design of the contour collimator being as compact as possible, comprising less mechanical transmission parts and provides a higher position accuracy. The term compact relates to a reduced assembly size of the contour collimator as well as the weight of the contour collimator.

This objective is attained in accordance with the invention by the subject-matter disclosed in the independent claim. Preferred embodiments which may be realized in an isolated way or in combination with other preferred embodiments are disclosed subsequently and in the dependent claims.

Thus, in a major aspect of the present invention, a contour collimator for radio therapy of the kind mentioned at the beginning is designed in such a way that the drive is a linear motor and each linear motor comprises a linearly movable rod directly fixed to each diaphragm element.

The term "directly fixed" as used herein refers to any fixation which does not involve a backlash. Such a direct fixation may be realized by screwing or welding the rod to the diaphragm element. Alternatively, the rod and diaphragm element may be integrally formed, which also represents a direct fixation.

The term "linear motor" as used herein refers to an electric motor that has had its stator and rotor unrolled so that instead of producing a torque or rotation, it directly produces a linear force along its length. Particularly, the linear drive of the present invention directly causes a translational movement of the rod which may be disposed with the drive coils. This translational movement is then directly transmitted to the diaphragm element due to the direct fixation of the rod to the diaphragm element. Linear motors may provide high acceleration values. The basic principle is in that the coils, which are arranged circularly in conventional rotative motors, are arranged along a linear distance, wherein the rotor, which rotates in conventional rotative motors, is pulled or attracted along the distance by the linearly moving magnetic field created by the coils.

Each linear motor and the associated diaphragm element may be arranged substantially within a common plane.

The term "substantially within a common plane" as used herein refers to an orientation which the skilled person would still consider as being within a common plane, i.e. an orientation with a deviation up to an amount of 1.0 mm compared to a strict orientation within a common plane.

The linear motors of a group of diaphragm elements may be arranged parallel to each other.

The term "parallel" as used herein refers to an orientation which the skilled person would consider as an orientation without any intersection.

Each linear motor may comprise a housing, wherein the rod is extendable through the housing. Thus, the rod may be at leas partially disposed within the housing and the rod may be extended from and retracted into the housing.

Each linear motor may comprise coils, wherein the rod may comprise magnets, wherein the rod is arranged so as to be linearly movable between the coils. Thus, a high accuracy for the movement control of the rod and the diaphragm element may be achieved as the provision of the rod with the magnets and the orientation of the coils allows an exact movement control.

The rod may be welded or screwed to the associated diaphragm element. This is a preferred design of the direct fixation, which clearly prevents any mechanical backlash.

Each diaphragm element may comprise a portion extended towards the associated linear motor, wherein the rod may be fixed to the extended portion. This facilitates the direct fixation of the rod to the diaphragm element.

The extended portion may comprise an angled portion located at an end facing the linear motor, wherein the rod may be fixed to the angled portion. This design clearly prevents any deviation from the movement or adjusting direction of the diaphragm element.

The linear motors of a group of diaphragm elements may be arranged in horizontal and vertical rows, wherein a vertical row of linear motors is associated with a sub-group of diaphragm elements adjacent to each other in a horizontal direction. This design is very compact.

The angled portions of a sub-group of diaphragm elements may be arranged at the same position in a horizontal direction.

The extended portions of a sub-group of diaphragm elements may be connected to the angled portions at positions shifted in a horizontal direction.

The rod may protrude from the linear motor in a direction facing away from the diaphragm element in a retracted position of the rod.

The linear drive may be designed to displace the associated diaphragm element in an adjusting direction and may additionally provide guidance to the diaphragm element with respect to any direction being oriented perpendicularly related to the adjusting direction. By combining the tasks to displace the diaphragm element in the adjusting direction and additionally provide aforesaid guidance to the diaphragm element within the linear drive, a collimator with compact design providing very precise and stable adjustability of the diaphragm element may be obtained.

The term "guidance" as used herein refers to a technical effect achieved by appropriate means which properly impedes the diaphragm element from deviating from the axis represented by the adjusting direction by a non-tolerable value.

The rod may extend substantially, i.e. with a deviation amounting up to ca.±10°, in the adjusting direction of the diaphragm element, i.e. the longitudinal axis of the guiding rod may substantially comply with the adjusting direction. Employing a guiding rod as proposed here yields several benefits. First of all, the diaphragm element which normally comprises heavy and expensive material may be of smaller length, as the guiding rod will provide sufficient range for the displacement of the diaphragm element. Consequently, the entire diaphragm element may be constructed lighter and more compact. Additionally, for the displacing and adjusting of the diaphragm element, a defined interaction of the linear drive with the guiding rod instead of the much larger diaphragm element may be envisaged, yielding a substantial advantage with regards to the precision of adjustment.

The rod may comprise ceramic material and/or the guiding rod may be coated with ceramic material. Said ceramic material has been found to exhibit an advantageous interaction with linear drive, as magnets, which interact with coils of the linear drive, may be attached to the rod.

The diaphragm element material may comprise a high density material, preferably tungsten. Tungsten has been found to have the capacity to very effectively shield beams from selected areas. A preferred embodiment of the diaphragm element material comprises sintered material comprising approximately 95% tungsten and further components, in particular iron and/or nickel and/or copper. Alternatively, diaphragm element materials with higher or lower fractions of tungsten compared to a preferred percentage of approximately 95% may be employed. Also, alternatively, a non-sintered material or even pure tungsten may be used as diaphragm element material. Generally, any material, in particular high density material, which has the capacity to shield beams, may be employed as diaphragm element material in order to implement the invention.

Two groups of diaphragm elements may be provided, wherein each group comprises a plurality of diaphragm elements according to the invention, and wherein the diaphragm elements of each group face each other. Consequently, by adjusting the diaphragm elements facing each other in their respective adjusting direction, an area of arbitrary shape, in particular any contour of a treatment object, for example a tumor, can be recreated for beam application.

Particularly, the present invention provides the following advantages. The collimator provides a reduction of the assembly size, weight and mechanical transmission parts. As the collimator uses a linear motor for displacing the diaphragm elements, an extremely high position accuracy is provided without mechanical loose effects. The linear motor allows a simplified control loop algorithm with no need to compensate looses and transmission. Further, the linear motor provides a reduction of dead time. The collimator achieves dynamic movements of the diaphragm elements up to 4 m/s in the patient plane. The direct fixation of the rod to the associated diaphragm element represents a simplified mechanical assembly and easier serviceability. Further, the direct fixation of the rod to the associated diaphragm element provides a reduction of friction loose and allows to omit transmission parts such as transmission gears. Still further, the direct fixation of the rod to the associated diaphragm element prevents mechanical backlash. A position sensor is already implemented in the linear drive such that an additional position sensor for primary position detection is not necessary. Particularly, the principle of the linear motor already implements an encoder system for the position detection. The collimator also allows the omission of a dead time compensation for control loop when driving sense changes. Contrary to other drive principle known in the prior art, no transmission of a rotary movement into a linear movement is required. The collimator also provides a simplified approach for establishing new treatment methods for tracking and gating, i.e. a compensation of tumor movement in realtime. More particularly, the collimator allows the establishment of new dynamic treatment requirements and a direct and dynamic control of movements to follow tumor movement without compensation of mechanical backlash. Still further, the linear drive provides independence of gravitation influences. Furthermore, the collimator provides a reduction of effort for fine adjustment and calibration needs for a sensor such as the position sensor. The linear drive used in the present invention allows a reduced noise in comparison to standard DC drives. The collimator also provides a high force/weight ratio.

Summarizing, the following embodiments are preferred embodiments of the present invention:

EMBODIMENT 1

A contour collimator for radiotherapy, comprising a plurality of plate-shaped diaphragm elements provided in a guiding block and movably arranged with respect to one another to form a contour diaphragm for a radiation beam emitted by a radiation source towards the collimator, and at least one drive for moving the diaphragm elements, wherein a drive of its own is associated with each diaphragm element, the drives of a group of diaphragm elements are arranged substantially adjacent to one another, and the drive is a linear motor, characterized in that each linear motor comprises a linearly movable rod directly fixed to each diaphragm element.

EMBODIMENT 2

The contour collimator according to the preceding embodiment, characterized in that each linear motor and the associated diaphragm element are arranged substantially within a common plane.

EMBODIMENT 3

The contour collimator according to any preceding embodiment, characterized in that the linear motors of a group of diaphragm elements are arranged parallel to each other.

EMBODIMENT 4

The contour collimator according to any preceding embodiment, characterized in that each linear motor comprises a housing, wherein the rod is extendable through the housing.

EMBODIMENT 5

The contour collimator according to the preceding embodiment, characterized in that each linear motor comprises coils, wherein the rod comprises magnets, wherein the rod is arranged so as to be linearly movable between the coils.

EMBODIMENT 6

The contour collimator according to any preceding embodiment, characterized in that the rod is welded or screwed to the associated diaphragm element.

EMBODIMENT 7

The contour collimator according to any preceding embodiment, characterized in that each diaphragm element comprises a portion extended towards the associated linear motor, wherein the rod is fixed to the extended portion.

EMBODIMENT 8

The contour collimator according to the preceding embodiment, characterized in that the extended portion comprises an angled portion located at an end facing the linear motor, wherein the rod is fixed to the angled portion.

EMBODIMENT 9

The contour collimator according to the preceding embodiment, characterized in that the linear motors of a group of diaphragm elements are arranged in horizontal and vertical rows, wherein a vertical row of linear motors is associated with a sub-group of diaphragm elements adjacent to each other in a horizontal direction.

EMBODIMENT 10

The contour collimator according to the preceding embodiment, characterized in that the angled portions of a sub-group of diaphragm elements are arranged at the same position in a horizontal direction.

EMBODIMENT 11

The contour collimator according to the preceding embodiment, characterized in that extended portions of a sub-group of diaphragm elements are connected to the angled portions at positions shifted in a horizontal direction.

EMBODIMENT 12

The contour collimator according to any preceding embodiment, characterized in that the rod protrudes from the linear motor in a direction facing away from the diaphragm element in a retracted position of the rod.

In the following, the invention will further be explained by way of both schematic and exemplary drawings. In the figures, identical reference numbers refer to identical components or components having the same or similar functions. Thus, such components and referring reference numbers might not be explained with regard to each figure, and explanations given on the occasion of preceding figures are referred to in such cases. In the figures, aspects of the collimator according to the invention will be explained referring to preferred embodiments. The exemplary embodiments related to in the figures and the referring explanations are merely given for illustrative purposes, and the invention is not restricted to these embodiments.

Shown are in

Figure 2:
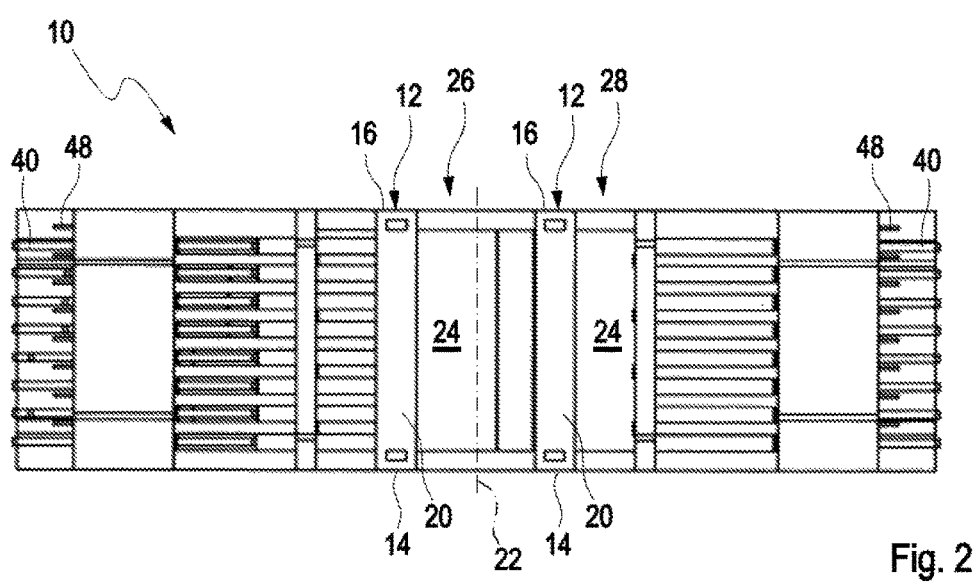
Figure 3:
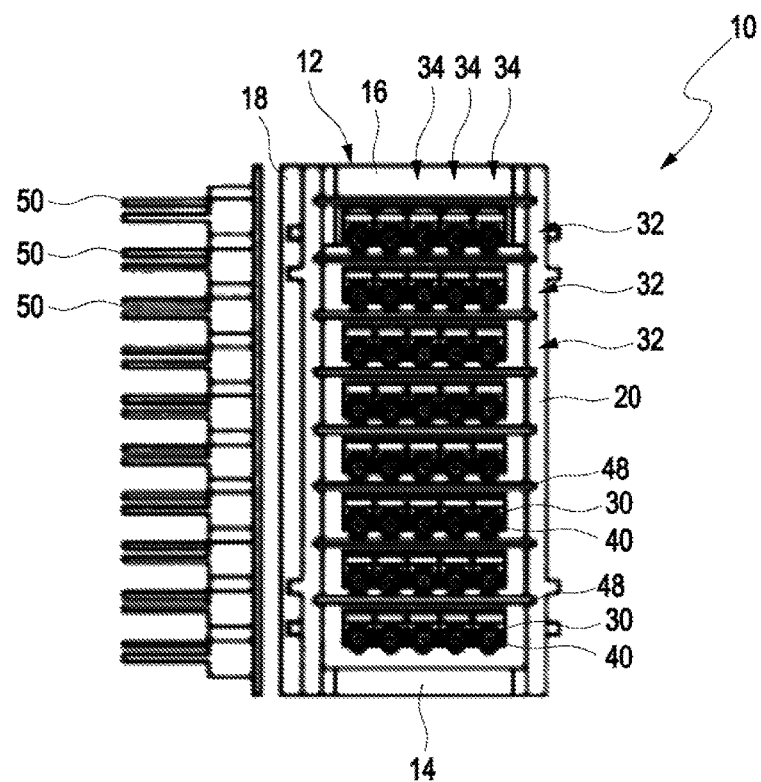
Figure 4:
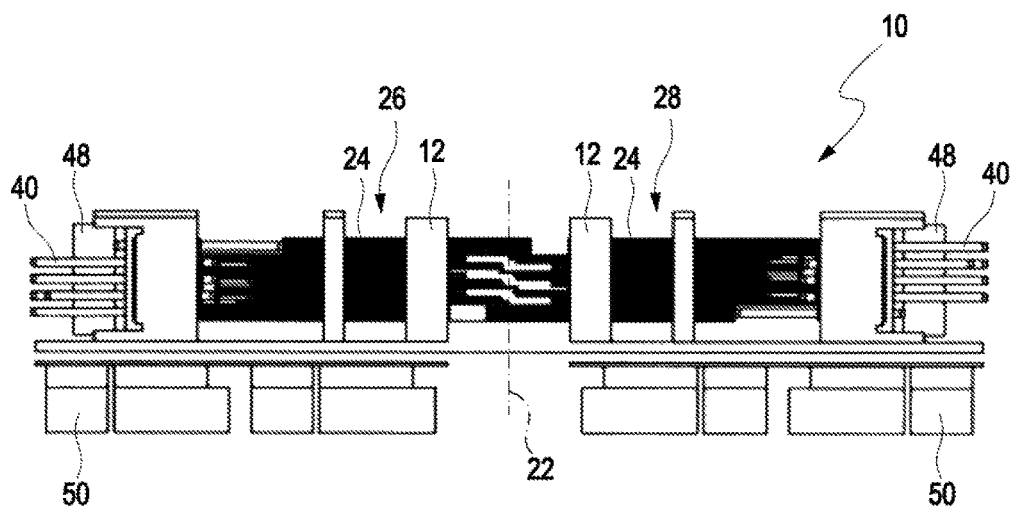
Figure 5:
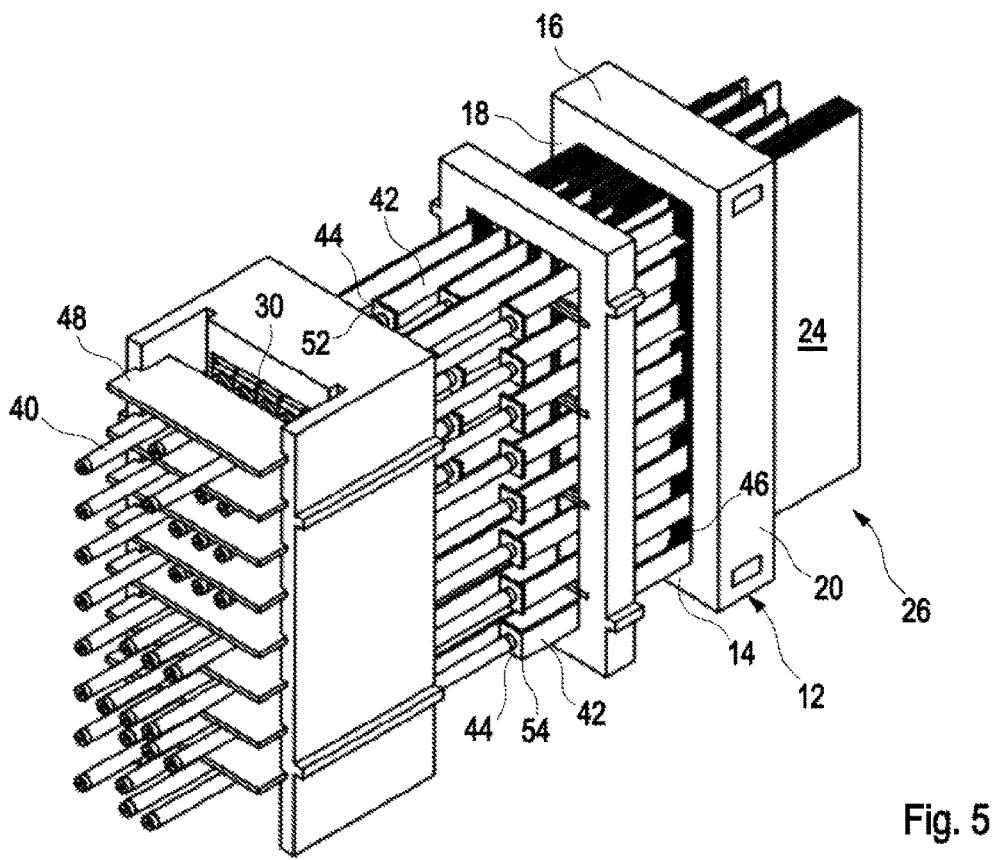
Figure 6:
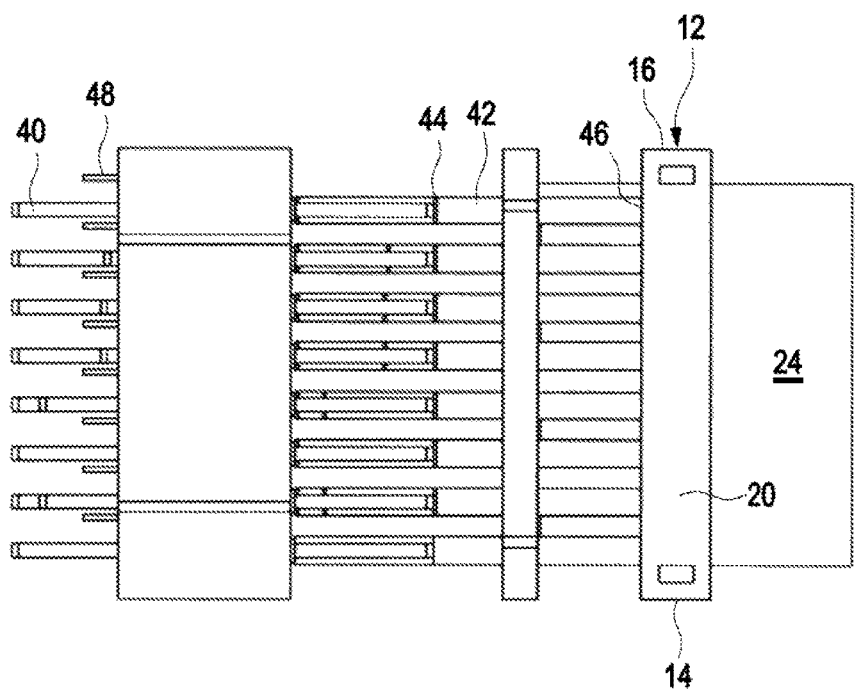
Figure 7:
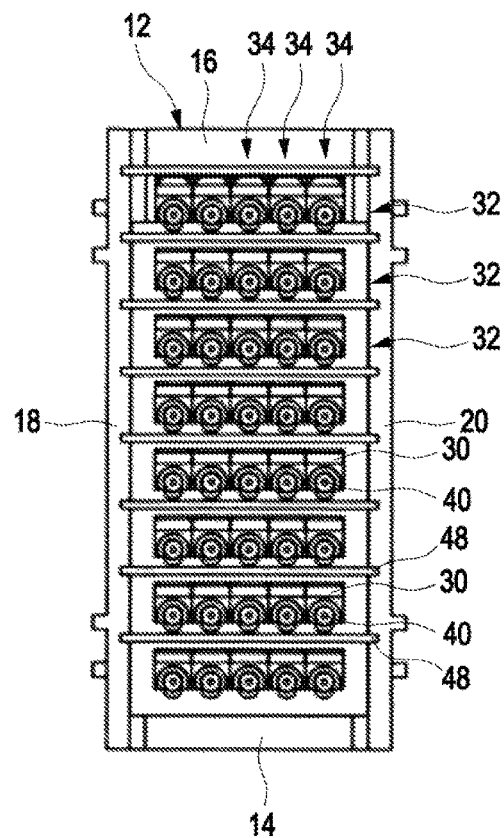
Figure 8:
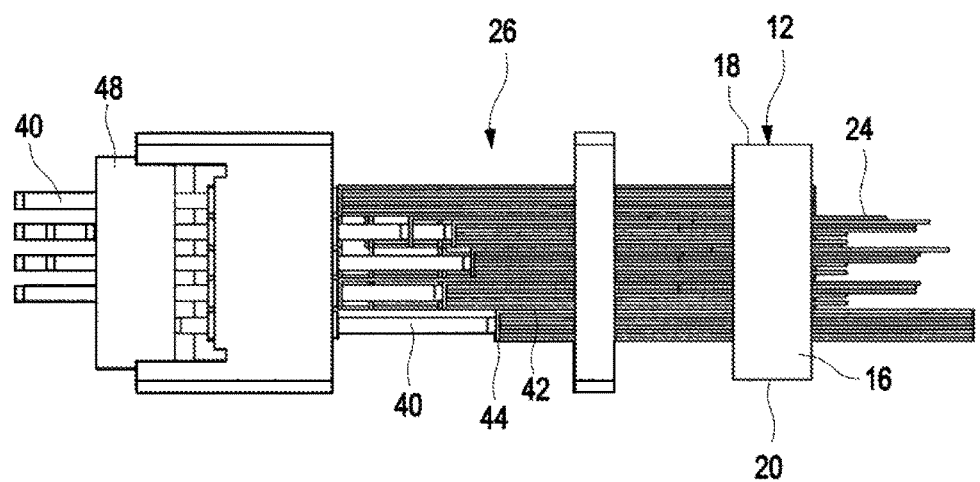
Figure 9:
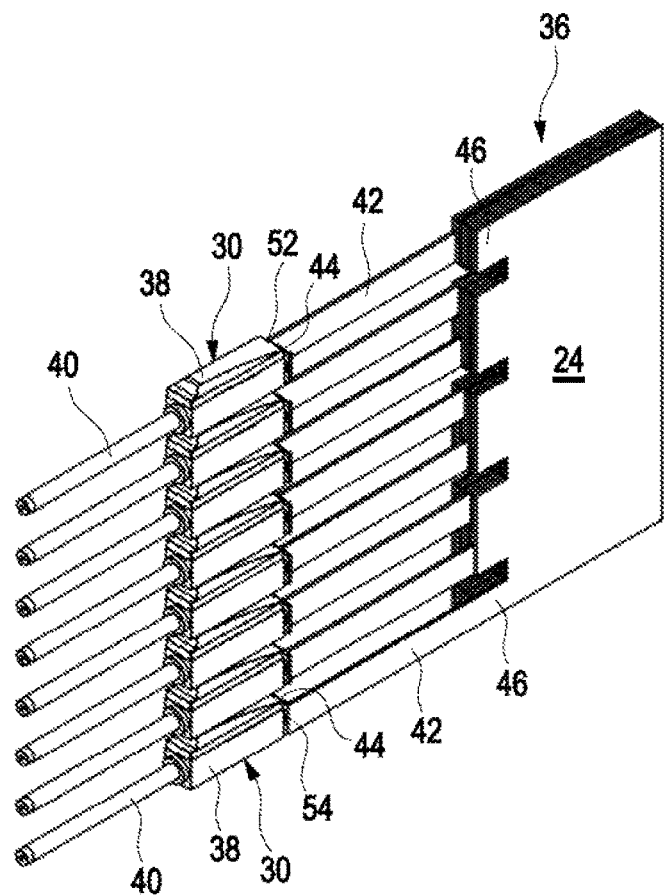
Figure 10:
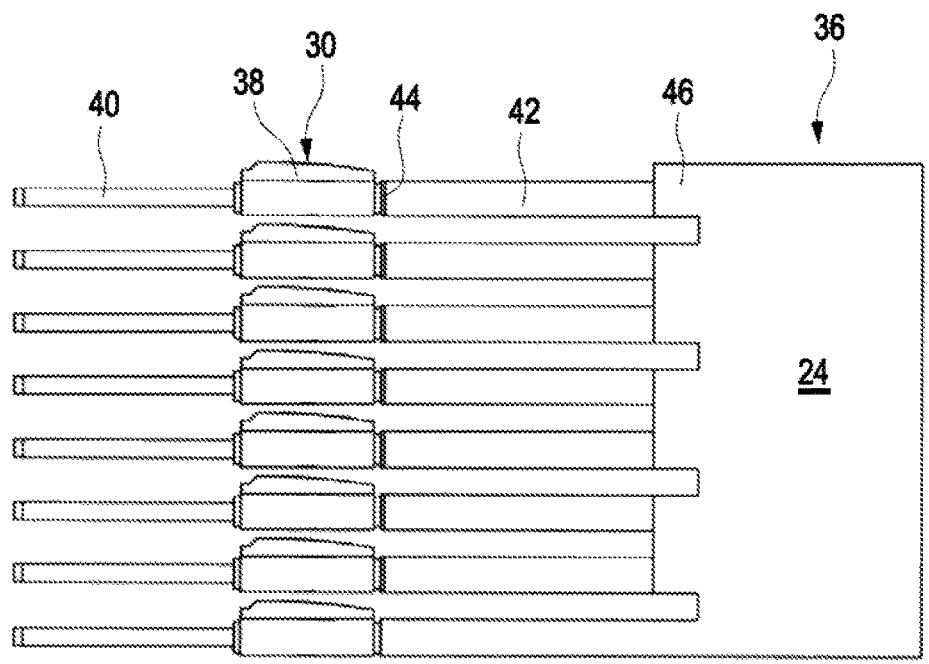
Figure 11:
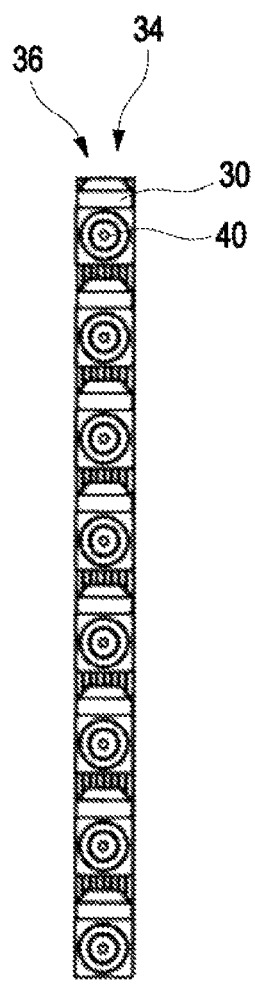
Figure 12:
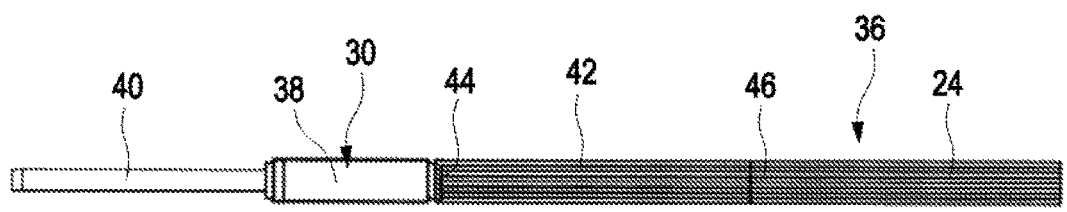

FIG. 1 a perspective view of a contour collimator according to the invention, FIG. 2 a front view of the contour collimator, FIG. 3 a left side view of the contour collimator, FIG. 4 a top view of the contour collimator, FIG. 5 a perspective view of a left portion of the contour collimator, FIG. 6 a font view of the left portion of the contour collimator, FIG. 7 a left side view of the left portion of the contour collimator, FIG. 8 a top view of the left portion of the contour collimator, FIG. 9 a perspective view of a group of diaphragm elements, FIG. 10 a front view of the group of diaphragm elements, FIG. 11 a left side view of the group of diaphragm elements, and FIG. 12 a top view of the group of diaphragm elements.

FIG. 1 is perspective view of a contour collimator 10 according to the present invention, whose core is formed by a guiding block 12. The guiding block 12 comprises a lower guide plate 14, an upper guide plate 16 as well as two side walls 18 and 20. The side walls 18, 20 connect the lower guide plate 14 and the upper guide plate 16 to one another. Thus, the guiding block 12 substantially comprises the shape of a rectangular frame. Needless to say, the collimator 10 may comprise further guiding blocks 12 or the guiding block 12 may be divided in several rectangular frame elements. The guiding block 12 may be covered at the upper side and the lower side by cover plates which respectively comprise an opening, which may be rectangular and provided centrally in the cover plates. The top side of the lower guide plate 16 is provided with a plurality of lower guide grooves extending in a longitudinal direction of the guiding block 12 and formed parallel to one another at equal lateral distance. The upper and lower guide plates 14, 16 are made preferably of brass, bronze or ceramics or another radiation-resistant material having good sliding properties. In the same way, upper guide grooves are provided on the bottom side of the upper guide plate 16. Since the guiding block 12 is made symmetrically with respect to a middle plane 22 extending perpendicular with respect to the longitudinal direction of guiding block 12 and through the center of openings in the upper and lower cover plates, only the design of the guiding block 12 on one side with respect to the middle plane 22 is described for the purpose of simplification. The design on the other side is formed analogously thereto.

Further, the contour collimator 10 comprises a plurality of plate-shaped diaphragm elements 24 which are provided in the guiding block 12 and movably arranged with respect to one another to form a contour diaphragm for a radiation beam emitted by a radiation source (not shown) towards the contour collimator 10. For this purpose, each of the diaphragm elements 24 is inserted in movably translatory fashion in each pairing of the vertically superposed guide grooves. The width of the individual guide grooves corresponds to about half the thickness of a diaphragm element 24. The thickness of a plate-shaped diaphragm element 24 may be about 1 mm. The diaphragm elements 24 inserted in the guide grooves are slightly spaced laterally, so that they do not come into contact. In order to allow the shielding of beams emitted by the radiation source, the diaphragm elements 24 comprise tungsten material. For example, the collimator 10 may comprise 40 diaphragm elements 24 on each side of the middle plane 22. Particularly, the diaphragm elements 24 on each side of the middle plane 22 respectively form a group 26, 28 of diaphragm elements 24.

FIG. 2 shows a front view of the contour collimator 10. Further, the contour collimator 10 comprises at least one drive 30 for moving the diaphragm elements 24. A drive 30 of its own is associated with each diaphragm element 24. The drives 30 of a group 26, 28 of diaphragm elements 24 are arranged substantially adjacent to one another. The drive 30 is a linear motor. More particularly, each linear motor 30 and the associated diaphragm element 24 are arranged substantially within a common plane. The linear motor may be a linear motor of the series LM1247 or LM2070 available from the company Dr. Fritz Faulhaber GmbH & Co. KG, Daimlerstraβe 23/25, 71101 Schönaich, Germany.

FIG. 3 shows a left side view of the contour collimator 10. As is shown, the linear motors 30 of a group 26, 28 of diaphragm elements 24 are arranged parallel to each other. More particularly, the linear motors 30 of a group 26, 28 of diaphragm elements 24 are arranged in horizontal and vertical rows 32, 34, wherein a vertical row 34 of linear motors 30 is associated with a sub-group 36 of diaphragm elements 24 adjacent to each other in a horizontal direction. The sub-group 36 of diaphragm elements 24 comprises 8 diaphragm elements 24 arranged directly adjacent to one another in the horizontal direction. Accordingly, on each side of the middle plane 22, there are 5 sub-groups 36 of diaphragm elements 24 The linear motor 30 comprises a housing 38. The linear motor 30 further comprises coils (not shown). The coils are disposed within the housing 38.

Each linear motor 30 also comprises a linear movable rod 40 directly fixed to the associated diaphragm element 24 as will be explained in more detail below. The rod 40 is extendable through the housing 38. For example, the rod 40 is welded or screwed to the associated diaphragm element 24. More particularly, each diaphragm element 24 comprises a portion 42 extended towards the associated linear motor 30. The rod 40 is fixed to the extended portion 42. For this purpose, the extended portion 42 comprises an angled portion 44 located at an end 46 facing the linear motor 30, wherein the rod 40 is fixed to the angled portion 44. The angled portions 44 of a sub-group 36 of diaphragm elements 24 are arranged at the same position in a horizontal direction. The extended portions 42 of a sub-group 36 of diaphragm elements 24 are connected to the angled portions 44 at positions shifted in a horizontal direction. The rod 40 protrudes from the linear motor 30 in a direction facing away from the diaphragm element 24 in a retracted position of the rod 40 as will be explained in more detail below.

The rod 40 comprises magnets (not shown). The magnets may be attached to the rod 40 on an outer surface thereof or may alternatively be disposed within the rod 40. The rod 40 is arranged so as to be linearly movable between the coils in the housing 38. Within the guiding block 12, position sensors (not shown) may be arranged for detecting the position of the diaphragm elements 24. A position sensor of its own may be associated with each diaphragm element 24. Each position sensor may be disposed so as to face the extended portion 42 of the associated diaphragm element 24. The position sensors are adapted to determine the position of the diaphragm elements 24 by measuring a magnetic field.

For example, the position sensors may be magnetic sensors, in particular Hall effect sensors. In this case, such a position sensor comprises a magnetic element adapted to provide a magnetic field, and a detector device capable of detecting said magnetic field, wherein the diaphragm element 24 comprises one of the magnetic element and the detector device, and the other of the magnetic element and the detector device is attached to a supporting device such as a part of the housing 38 relative to which the diaphragm element 24 is movable. In particular, the diaphragm element 24 may comprise at least part of the measurement device. Preferably, the part of the measurement device may be integrated into the diaphragm element 24, in particular milled into the diaphragm element 24. This allows to provide the diaphragm element 24 with the measurement device with minimal impact on the operability of the collimator. Alternatively, the part of the measurement device may be attached to the diaphragm element 24, in particular mounted onto a surface of the diaphragm element 24 or glued to the diaphragm element 24 such as the extended portion 42. Since the magnetic sensor is small, it may be attached to the outer surface of the diaphragm element 24 without affecting the operability of the collimator system. Further, magnetic sensors also allow for contact-free measurements, and therefore measurement results are not affected by friction or abrasive wear. Alternatively, instead of an analog Hall effect sensor, sine/cosine type Hall effect sensors may be used with the present invention. Such position sensors match user's positioning needs without requiring an external encoder. Additional sensors such as potentiometers may be equipped within the design. Examples for apparatus and methods for detecting the position of the diaphragm elements 24 are described in WO2012/123093 A1, the contents of which relating to methods and apparatus for position sensoring such as magnetic encoders are incorporated herein by reference.

Further, adjacent the linear motors 30, boards 48 may be disposed for supporting circuit boards and other electrical connections (not shown) necessary for activating the linear motors 30. At the outer side of the guiding block 12, control means 50 such as electronic control units for controlling the linear motors 30 are provided.

FIG. 4 shows a top view of the contour collimator 10. Particularly, this drawing is very explicit in showing that within contour collimator 10, adjacent diaphragm elements 24 may be stacked in such a way that a shielding of beams from a selected area to form a contour diaphragm can be implemented.

FIG. 5 shows a perspective view of a left portion of the contour collimator 10. As mentioned above, the angled portions 44 of a sub-group 36 of diaphragm elements 24 are arranged at the same position in a horizontal direction. The extended portions 42 of a subgroup 36 of diaphragm elements 24 are connected to the angled portions 44 at positions shifted in a horizontal direction. FIG. 5 exemplarily shows that the extended portion 42 of the uppermost diaphragm element 24 of a sub-group 36 is connected to the opposite end of the angled portion 44 than the extended portion 42 of the lowermost diaphragm element 24 of the same sub-group 36. In the example of FIG. 5, the extended portion 42 of the uppermost diaphragm element 24 of a sub-group 36 is connected to the left end 52 of the angled portion 44 if seen from the left to the right in FIG. 5, whereas the extended portion 42 of the lowermost diaphragm element 24 of the same sub-group 36 is connected to the right end 54 of the angled portion 44. The extended portions 42 of diaphragm elements 24 of the same sub-group 36 are connected to the angled portions 44 at intermediate positions between the left end and right end shifted in the horizontal direction. This shifting in the positions of the extended portions 42 in the horizontal direction allows to arrange the diaphragm elements 24 in a very compact manner as the angled portions 44 do not obstruct each other. FIG. 5 further shows that the linear motors 30 may be individually activated so as to displace the associated diaphragm element 24 in order to form the contour diaphragm.

FIG. 6 shows a front view of the left portion of the contour collimator 10. Particularly, this drawing is very explicit in showing that within contour collimator 10, the rods 40 protrude from the linear motors 30 in a direction facing away from the diaphragm elements 24 in a retracted position of the rods 40.

FIG. 7 shows a left side view of the left portion of the contour collimator 10. Particularly, this drawing is very explicit in showing that within contour collimator 10, the linear motors 30 are arranged in horizontal rows 32 and vertical rows 34. In the example shown in FIG. 7, there are 8 horizontal rows 32 and 5 vertical rows 34.

FIG. 8 shows a top view of the left portion of the contour collimator 10. Particularly, this drawing is very explicit in showing that within contour collimator 10, the linear motors 30 may be individually activated so as to displace the associated diaphragm element 24 in order to form the contour diaphragm. Further, FIG. 8 shows the arrangement of the diaphragm elements 24 in a very compact manner as the angled portions 44 do not obstruct each other.

FIG. 9 shows a perspective view of a sub-group 36 of diaphragm elements 24 to which rods 40 of the linear motors 30 are directly fixed. As explained with reference to FIG. 5, the angled portions 44 of the sub-group 36 of diaphragm elements 24 are arranged at the same position in a horizontal direction. The extended portions 42 of a sub-group 36 of diaphragm elements 24 are connected to the angled portions 44 at positions shifted in a horizontal direction. FIG. 5 exemplarily shows that the extended portion 42 of the uppermost diaphragm element 24 of a sub-group 36 is connected to the opposite end of the angled portion 44 than the extended portion 42 of the lowermost diaphragm element 24 of the same sub-group 36. FIG. 9 also shows that the extended portions 42 of the sub-group 36 of diaphragm elements 24 are arranged at the shifted positions in a vertical direction. In the example shown in FIG. 9, the rod 40 of uppermost linear motor 30 is connected to the uppermost extended portion 42 of the left diaphragm element 24 of the sub-group 36 and the rod 40 of lowermost linear motor 30 is connected to lowermost extended portion 42 of the right diaphragm element 24 of the sub-group 36 if seen from the left to the right in FIG. 9.

FIG. 10 shows a front view of the sub-group 36 of diaphragm elements 24. Particularly, this drawing is very explicit in showing that within contour collimator 10, the rods 40 protrude from the linear motors 30 in a direction facing away from the diaphragm elements 24 in a retracted position of the rods 40.

FIG. 11 shows a left side view of the sub-group 36 of diaphragm elements 24. Particularly, this drawing is very explicit in showing that within contour collimator 10, the linear motors 30 of the sub-group 36 are arranged in a vertical row 34. In the example shown in FIG. 11, there are 8 linear motors 30 in the vertical row 34.

FIG. 12 shows a top view of the sub-group 36 of diaphragm elements 24. Particularly, this drawing is very explicit in showing that within contour collimator 10, the linear motors 30 may be arranged in a compact manner as the linear motors 30 of the sub-group 36 may be arranged in a vertical row 34. Further, FIG. 12 shows the arrangement of the diaphragm elements 24 in a very compact manner as the angled portions 44 do not obstruct each other. As is shown in FIG. 12, the sub-group 36 comprises 8 diaphragm elements 24 arranged parallel and adjacent to one another in the horizontal direction.

As mentioned above, in order to displace a diaphragm element 24 in an adjusting direction for forming the contour diaphragm, the linear motor 30 associated with the diaphragm element 24. Particularly, the linear motor 24 is supplied with electric current or electric voltage. The electric current or electric voltage creates a magnetic field around the coil within the housing 38. The magnetic field causes the rod 40 of the linear motor 30 to extend or retract through the housing 38 depending on the direction of the magnetic field. This extension or retraction of the rod 40 causes the diaphragm element 24 to which the rod 40 is directly fixed to extend or retract. By individually activating the linear motors 30, the individual diaphragm elements 24 are displaced in the adjusting direction to form the contour diaphragm corresponding to the treatment object to be irradiated. The exact position of the diaphragm element 24 is detected by the position sensor. As the rod 40 of the linear motor 30 is directly fixed to the diaphragm element 24, an additional position sensor, i.e. a secondary position sensor, for compensating a backlash as with conventional electric drives is not necessary as the direct fixation prevents any backlash.

LIST OF REFERENCE SYMBOLS 10 contour collimator
12 guiding block
14 lower guide plate
16 upper guide plate
18 side wall
20 side wall
22 middle plane
24 diaphragm elements
26 group of diaphragm elements
28 group of diaphragm elements
30 drive/linear motor
32 horizontal row
34 vertical row
36 sub-group
38 housing
40 rod
42 extended portion
44 angled portion
46 end
48 board
50 control means
52 left end
54 right end

The invention claimed is:

1. A contour collimator for radiotherapy, comprising
a plurality of plate-shaped diaphragm elements provided in a guiding block and movably arranged with respect to one another to form a contour diaphragm for a radiation beam emitted by a radiation source towards the collimator, and
at least one drive for moving the diaphragm elements, wherein
each diaphragm element is associated with its own drive of the at least one drive, the drives of a group of diaphragm elements are arranged substantially adjacent to one another, and each drive is a linear motor, wherein
each linear motor comprises a linearly movable rod directly fixed to the associated diaphragm element,
wherein the linear motors of a group of diaphragm elements are arranged in horizontal and vertical rows, a vertical row of linear motors is associated with a sub-group of diaphragm elements adjacent to each other in a horizontal direction,
wherein each diaphragm element comprises a portion extended towards an associated linear motor, the extended portion comprises an angled portion located at an end facing the linear motor, wherein an associated rod is fixed to the angled portion,
wherein extended portions of a sub-group of the diaphragm elements are connected to the angled portions at positions shifted in a horizontal direction, and
wherein extended portions of a sub-group of the diaphragm elements are offset from a longitudinal axis of the associated rods.

2. The contour collimator according to claim 1, wherein each linear motor and the associated diaphragm element are arranged substantially within a common plane.

3. The contour collimator according to claim 1, wherein the linear motors of a group of diaphragm elements are arranged parallel to each other.

4. The contour collimator according to claim 1, wherein each linear motor comprises a housing, wherein the rod is extendable through the housing.

5. The contour collimator according to claim 1, wherein each linear motor comprises coils, wherein the rod comprises magnets, wherein the rod is arranged so as to be linearly movable between the coils.

6. The contour collimator according to claim 1, wherein the rod is welded or screwed to the associated diaphragm element.

7. The contour collimator according to claim 1, wherein the angled portions of a sub-group of diaphragm elements are arranged at the same position in a horizontal direction.

8. The contour collimator according to claim 1, wherein the rod protrudes from the linear motor in a direction facing away from the diaphragm element in a retracted position of the rod.

\* \* \* \* \*